(12) United States Patent
Cunningham et al.

(10) Patent No.: US 8,480,726 B2
(45) Date of Patent: Jul. 9, 2013

(54) STENT GRAFT WITH VALVE ARRANGEMENT

(75) Inventors: Kylie F. Cunningham, Carine (AU); Werner Dieter Ducke, Eight Mile Plains (AU); David Ernest Hartley, Wannanup (AU); Chantelle King, Kelvin Grove (AU); Blayne A. Roeder, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/405,919

(22) Filed: Feb. 27, 2012

(65) Prior Publication Data
US 2012/0221094 A1   Aug. 30, 2012

(30) Foreign Application Priority Data

Feb. 28, 2011 (AU) .............................. 2011200858

(51) Int. Cl.
*A61F 2/06* (2006.01)
(52) U.S. Cl.
USPC ..................................... 623/1.13; 623/1.35
(58) Field of Classification Search
USPC ............... 623/1.11, 1.12, 1.13, 1.14, 1.16, 623/1.23, 1.24, 1.27, 1.35; 604/9
See application file for complete search history.

(56) References Cited

U.S. PATENT DOCUMENTS

| | | | |
|---|---|---|---|
| 4,902,508 A | 2/1990 | Badylak et al. | |
| 5,711,969 A | 1/1998 | Patel et al. | |
| 5,733,337 A | 3/1998 | Carr, Jr. et al. | |
| 5,885,619 A | 3/1999 | Patel et al. | |
| 5,955,110 A | 9/1999 | Patel et al. | |
| 5,968,096 A | 10/1999 | Whitson et al. | |

(Continued)

FOREIGN PATENT DOCUMENTS

| | | |
|---|---|---|
| JP | 2003250907 | 9/2003 |
| WO | 9822158 A3 | 5/1998 |

(Continued)

OTHER PUBLICATIONS

Tam Huynh, Ginger Abraham, James Murray, Kelvin Brockbank, Per-Otto Hagen, and Susan Sullivan, Remodeling of an acellular collagen graft into a physiologically responsive neovessel, Nature Biotechnology vol. 17, Nov. 1999, pp. 1083-1086.

*Primary Examiner* — Corrine M McDermott
*Assistant Examiner* — Robert A Lynch
(74) *Attorney, Agent, or Firm* — Richard J. Godlewski

(57) ABSTRACT

A stent graft (10) has a tubular body with a side aperture (16) covered by a valve arrangement (18) and an arrangement to hold the valve open (32) with a release wire (30). Retraction of the release wire closes the valve. The stent graft can have a tubular body with a first bifurcation (134) with first and second legs (130, 132) extending from the bifurcation. The side aperture and valve arrangement can be in one of the legs. One of the legs (132) has a further bifurcation (142) to define a side arm (140). The stent graft can be deployed into the vasculature of a patient with the tubular body being in an aorta of the patient, a first leg extending down an iliac artery, a second leg being directed towards a contralateral iliac artery and the side arm directed to an internal artery of the contralateral iliac artery.

20 Claims, 5 Drawing Sheets

U.S. PATENT DOCUMENTS

| | | |
|---|---|---|
| 8,012,193 B2 | 9/2011 | Hartley et al. |
| 2002/0169497 A1 | 11/2002 | Wholey et al. |
| 2003/0204243 A1 | 10/2003 | Shiu |
| 2004/0059406 A1 | 3/2004 | Cully et al. |
| 2005/0059923 A1 | 3/2005 | Gamboa |
| 2006/0247761 A1 | 11/2006 | Greenberg et al. |
| 2006/0287712 A1 | 12/2006 | Eidenschink |
| 2007/0123910 A1 | 5/2007 | Hartley et al. |
| 2007/0250154 A1 | 10/2007 | Greenberg et al. |
| 2008/0147163 A1 | 6/2008 | Allen |

FOREIGN PATENT DOCUMENTS

| | | |
|---|---|---|
| WO | 98/53761 A1 | 12/1998 |
| WO | 2008057568 A1 | 5/2008 |
| WO | 2008057569 A1 | 5/2008 |

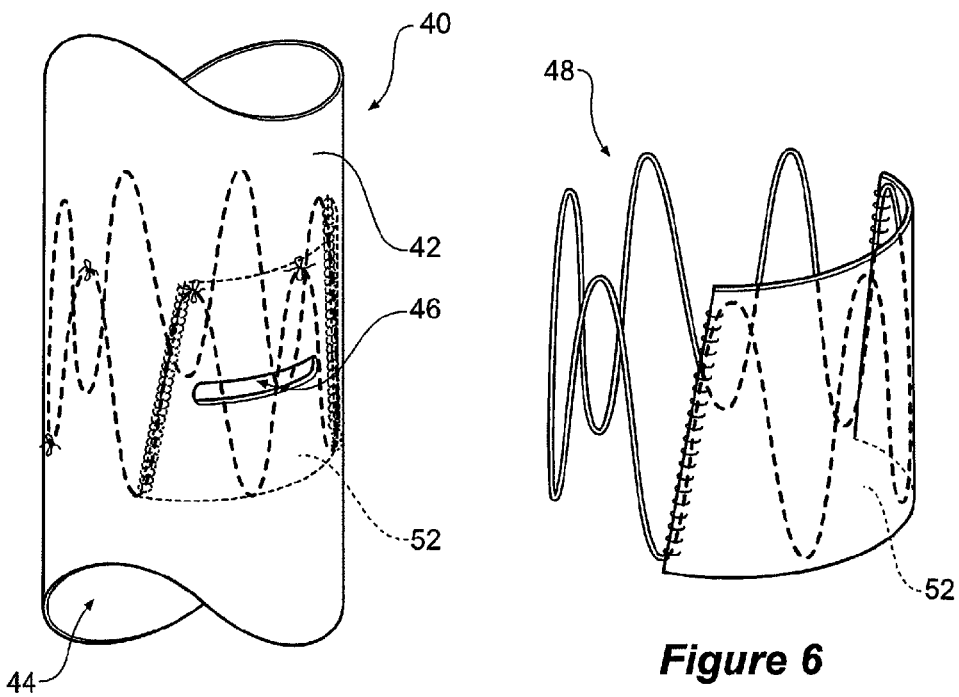
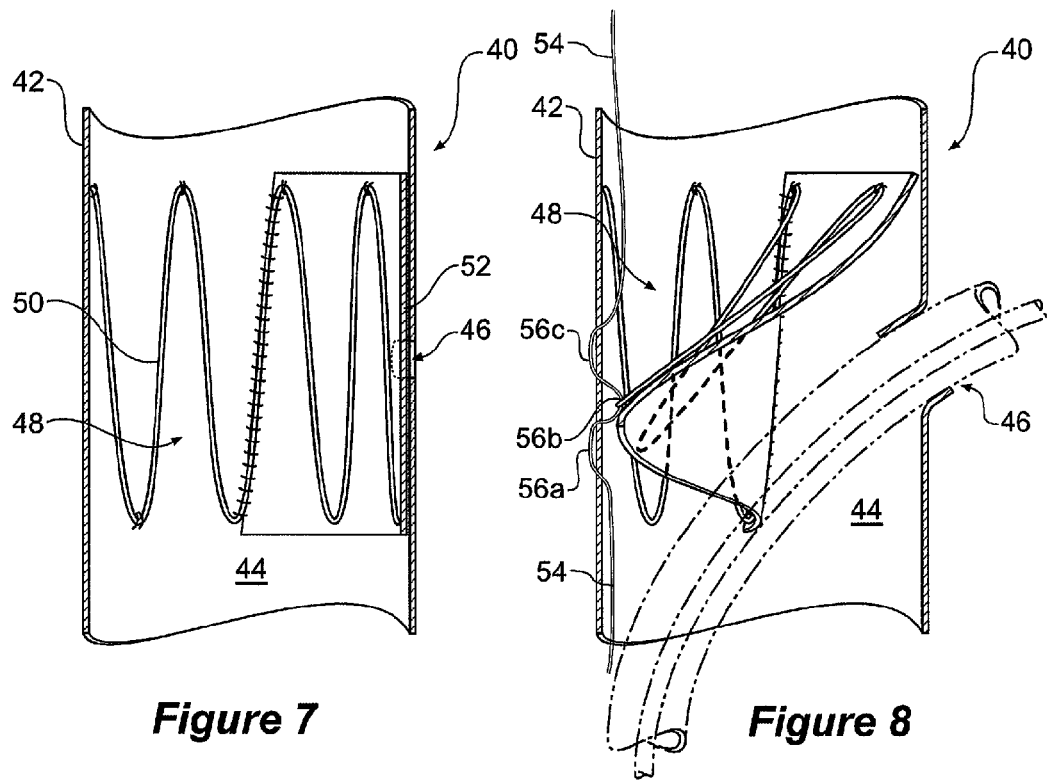

STENT GRAFT WITH VALVE ARRANGEMENT

INCORPORATION BY REFERENCE

The following co-pending patent applications are referred to in the following description:

U.S. patent application Ser. No. 10/962,763 entitled "Introducer for Iliac Side Branch Device".

PCT Patent Publication No. WO 98/53761 entitled "A Prosthesis and a Method of Deploying a Prosthesis"

U.S. patent application Ser. No. 11/600,655 entitled "Stent Graft Introducer" (U.S. Publication 2007/0123910)

U.S. patent application Ser. No. 11/788,285 entitled "Twin Bifurcated Stent Graft" (U.S. Publication 2007/0250154)

The entire content of each of these applications is hereby incorporated by reference.

TECHNICAL FIELD

This invention relates to a medical device and more particularly a device which can be deployed by endovascular means into the vasculature of a patient.

BACKGROUND OF THE INVENTION

Endovascular devices such a stent graft are use to repair defects in the vasculature if a patient. In some procedures it is necessary to provide a valve arrangement in the wall of a stent graft to allow temporary access during introduction of the endovascular device.

An object of this invention is to provide a valve arrangement in such situations or at least provide a physician with a useful alternative. There have been proposed bifurcated endovascular devices which can be deployed into the vasculature, particularly in the region of the aortic bifurcation, so that an aneurysm in the aorta can be bridged by placement of the endovascular device. In use a proximal portion of such a device seals into a non-aneurysed portion of the aorta adjacent to the renal arteries, a first leg extends down one iliac artery to a non-aneurysed portion of the iliac artery and another short leg extends towards the contra-lateral iliac artery. A leg extension may be placed to extend from the short leg into a non-aneurysed portion of the contra-lateral iliac artery.

There can be problems, however, if the aneurysm of the aorta extends down into one or other of the iliac arteries. Each of the common iliac arteries branches into the internal and external iliac arteries and it is necessary in such a situation that a blood flow path can be directed through an endovascular stent graft into each of these arteries.

The further object of this invention is to provide a single endovascularly deployed medical device which can solve this problem or at least provide a physician with a useful alternative.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

In one form therefore the invention is said to reside in a stent graft delivery device in combination with a stent graft, the stent graft comprising a tubular body of a biocompatible graft material defining a lumen therethrough, the tubular body comprising a side aperture and a valve arrangement associated with the tubular body to prevent fluid flow through the aperture from inside of the tubular body to outside of the tubular body, the stent graft delivery device comprising a distal end of the delivery device to remain outside a patient in use and a proximal end of the delivery device to be introduced into a patient in use, an arrangement to retain the stent graft on the introducer device adjacent to the proximal end of the delivery device, the distal end of the delivery device comprising a release wire mechanism and a release wire extending from the release wire mechanism towards and into the main lumen of the stent graft and engaging the valve arrangement to hold the valve arrangement away from the side aperture, whereby activation of the release wire mechanism retracts the release wire and releases the valve arrangement such that the valve arrangement closes off the side aperture.

Preferably the stent graft delivery device comprising a guide wire catheter, the guide wire catheter extending from the distal end of the delivery device to the proximal end of the delivery device, a pusher catheter over the guide wire catheter and extending from the distal end of the delivery device to a proximal pusher catheter end, the pusher catheter comprising a pusher lumen and the guide wire catheter extending through the pusher lumen, a nose cone dilator on the guide wire catheter at the proximal introducer end and the stent graft being retained on the introducer device distally of the nose cone dilator and proximally of the proximal pusher end, the release wire mechanism extending through the pusher lumen and into the main lumen of the stent graft to engage the valve arrangement.

Preferably the side aperture comprises a transverse slit in the tubular body.

Preferably the valve arrangement comprises a sleeve of a biocompatible graft material within the tubular body and a self expanding stent within the sleeve, the sleeve being fastened at its proximal end to the tubular body proximally of the aperture and the self expanding stent being fastened to the sleeve, whereby the self expanding stent forces the sleeve against the inner surface of the first leg around the aperture to prevent fluid flow through the aperture from inside of the leg to outside of the leg. The sleeve of a biocompatible graft material can comprise a cylindrical form. Alternatively the sleeve of a biocompatible graft material can comprise a semi-cylindrical form.

Preferably the valve arrangement comprises a self expanding stent to which a part cylindrical portion of biocompatible graft material is stitched along spaced apart struts of the self expanding stent, the self expanding stent and sleeve being fastened at their proximal ends to the tubular body proximally of the aperture.

Preferably the engagement of the release wire with the valve arrangement comprises the release wire being stitched into the graft material of the tubular body and then into the valve arrangement and then into the graft material of the tubular body again.

Preferably the engagement of the release wire with the graft material of the tubular body comprises stitching the release wire into the graft material at a position on the tubular body substantially opposite to the side aperture.

Preferably the valve arrangement comprises a self expanding stent and a sleeve of biocompatible graft material and the engagement of the release wire with the valve arrangement comprises stitching the release wire around a strut or apex of the self expanding stent.

In an alternative form the invention comprises a stent graft delivery device in combination with a stent graft, the stent graft comprising a tubular body of a biocompatible graft material defining a main lumen therethrough, a bifurcation in the tubular body at one end thereof and a first leg and a second leg extending from the bifurcation, the first leg being a long leg and the second leg being a short leg, the first and second legs having respective first and second lumens therethrough and the first and second lumens being in fluid communication with the main lumen, the first leg comprising a side arm with a side arm lumen therethrough and the side arm lumen being in fluid communication with the first leg lumen, the first leg comprising a side aperture and a valve arrangement to prevent fluid flow through the aperture from inside of the leg to outside of the leg, the side aperture comprising a transverse slit, the stent graft delivery device comprising a distal end intended to remain outside a patient in use and a proximal end to be introduced into a patient in use, the stent graft delivery device comprising a guide wire catheter, the guide wire catheter extending from a distal introducer end to a proximal introducer end, a pusher catheter over the guide wire catheter and extending from the distal introducer end to a proximal pusher end, the pusher catheter comprising a pusher lumen and the guide wire catheter extending through the pusher lumen, a nose cone dilator on the guide wire catheter at the proximal introducer end and an arrangement to retain the stent graft on the introducer device distally of the nose cone dilator and proximally of the proximal pusher end, the guide wire catheter extending through the first leg lumen and the main lumen of the main tubular body, the distal end of the delivery device comprising a release wire mechanism and a release wire extending from the release wire mechanism through the pusher lumen and into the first lumen of the stent graft and engaging the valve arrangement to hold the valve arrangement away from the side aperture, whereby activation of the release wire mechanism retracts the release wire and releases the valve arrangement such that the valve arrangement closes off the side aperture.

Preferably the valve arrangement comprises a sleeve of a biocompatible graft material within the tubular body and a self expanding stent within the sleeve, the sleeve being fastened at its proximal end to the tubular body proximally of the aperture and the self expanding stent being fastened to the sleeve, whereby the self expanding stent forces the sleeve against the inner surface of the first leg around the aperture to prevent fluid flow through the aperture from inside of the leg to outside of the leg. The sleeve of a biocompatible graft material can comprise a cylindrical form. Alternatively the sleeve of a biocompatible graft material can comprise a semi-cylindrical form.

Preferably the valve arrangement comprises a valve assembly comprising a self expanding stent to which a part cylindrical portion of biocompatible graft material is stitched along spaced apart struts of the self expanding stent, the self expanding stent and sleeve being fastened at their proximal ends to the tubular body proximally of the aperture.

Preferably the engagement of the release wire with the valve arrangement comprises the release wire being stitched into the graft material of the first leg and then into the valve arrangement and then into the graft material of the first leg again.

Preferably the engagement of the release wire with the graft material of the first leg comprises stitching the release wire into the graft material at a position on the first leg substantially opposite to the side aperture.

Preferably the valve arrangement comprises a self expanding stent and a sleeve of biocompatible graft material and the engagement of the release wire with the valve arrangement comprises stitching the release wire around a strut of the self expanding stent.

Preferably the stent graft delivery device further includes an indwelling catheter extending from the distal introducer end through the pusher lumen in the pusher catheter to the stent graft, the indwelling catheter exiting from the pusher lumen at a distal end of the branched stent graft, the indwelling catheter then extending along and outside of the first long leg of the stent graft and then entering the distal open end of the side arm, the indwelling catheter then extending through the side arm lumen to the first leg lumen and then extending out of the side aperture and then extending outside and along the tubular body of the stent graft to the nose cone dilator, the indwelling catheter having an indwelling guide wire extending therethrough, whereby the indwelling guide wire can be extended beyond the nose cone dilator in use, whereby the stent graft can be deployed into the vasculature of a patient with the tubular body being in an aorta of the patient, the first leg extending down a common iliac artery, the second leg being directed towards a contra-lateral common iliac artery and the side arm on the first leg directed to an internal iliac artery of the ipsilateral common iliac artery.

In an alternative form the invention comprises a stent graft delivery device in combination with a stent graft, the stent graft comprising a tubular body of a biocompatible graft material defining a main lumen therethrough, a bifurcation in the tubular body at one end thereof and a first leg and a second leg extending from the bifurcation, the first leg being a long leg and the second leg being a short leg, the first and second legs having respective first and second lumens therethrough and the first and second lumens being in fluid communication with the main lumen, the first long leg comprising a side arm with a side arm lumen therethrough and the side arm lumen being in fluid communication with the first leg lumen, the first leg comprising a side aperture and a valve arrangement to prevent fluid flow through the aperture from inside of the leg to outside of the leg, the side aperture comprising a transverse slit, the stent graft delivery device comprising a distal end intended to remain outside a patient in use and a proximal end to be introduced into a patient in use, the stent graft delivery device comprising a guide wire catheter, the guide wire catheter extending from a distal introducer end to a proximal introducer end, a pusher catheter over the guide wire catheter and extending from the distal introducer end to a proximal pusher end, the pusher catheter comprising a pusher lumen and the guide wire catheter extending through the pusher lumen, a nose cone dilator on the guide wire catheter at the proximal introducer end and an arrangement to retain the stent graft on the introducer device distally of the nose cone dilator and proximally of the proximal pusher end, the guide wire catheter extending through the first leg lumen and the main lumen of the main tubular body, an indwelling catheter extending from the distal introducer end through the pusher lumen in the pusher catheter to the stent graft, the indwelling catheter exiting from the pusher lumen at a distal end of the branched stent graft, the indwelling catheter then extending along and outside of the first long leg of the stent graft and then entering the distal open end of the side arm, the indwelling catheter then extending through the side arm lumen to the first leg lumen and then extending out of the side aperture and then extending outside and along the tubular body of the stent graft to the nose cone dilator, the indwelling catheter having an indwelling guide wire extending therethrough, whereby the indwelling guide wire can be extended beyond the nose cone dilator in use, the distal end of the delivery device comprising a release wire mechanism and a release wire extending from the release wire mechanism through the pusher lumen and into the first lumen of the stent graft and engaging the valve arrangement to hold the valve arrangement away from the side aperture, the engagement of the release wire with the valve arrangement comprises the release wire being stitched into the graft material of the first leg and then into the valve arrangement and then into the graft material of the first leg again.

whereby activation of the release wire mechanism retracts the release wire and releases the valve arrangement such that the valve arrangement closes off the side aperture.

The biocompatible graft material can include polytetrafluoroethylene, Dacron, polyamide or any other suitable biocompatible graft material. While Dacron, expanded polytetrafluoroethylene (ePTFE), or other synthetic biocompatible materials can be used for the tubular graft material for the stent graft, a naturally occurring biomaterial, such as collagen, is highly desirable, particularly a specially derived collagen material known as an extracellular matrix (ECM), such as small intestinal submucosa (SIS). Besides SIS, examples of ECM's include pericardium, stomach submucosa, liver basement membrane, urinary bladder submucosa, tissue mucosa, and dura mater. SIS is particularly useful, and can be made in the fashion described in Badylak et al., U.S. Pat. No. 4,902,508; Intestinal Collagen Layer described in U.S. Pat. No. 5,733,337 to Carr and in 17 Nature Biotechnology 1083 (November 1999); Cook et al., WIPO Publication WO 98/22158, dated 28 May 1998, which is the published application of PCT/US97/14855, the teachings of which are incorporated herein by reference. Irrespective of the origin of the material (synthetic versus naturally occurring), the material can be made thicker by making multilaminate constructs, for example SIS constructs as described in U.S. Pat. Nos. 5,968,096; 5,955,110; 5,885,619; and 5,711,969. In addition to xenogenic biomaterials, such as SIS, autologous tissue can be harvested as well, for use in forming the tubular graft material. Additionally Elastin or Elastin-Like Polypetides (ELPs) and the like offer potential as a material to fabricate the tubular graft material to form a device with exceptional biocompatibility.

SIS is available from Cook Biotech, West Lafayette, Ind., USA. U.S. patent application Ser. No. 11/788,285 entitled "Twin Bifurcated Stent Graft" (US Publication 2007/0250154) describes the use of a bifurcated graft which includes a further bifurcation on one of its legs to enable cathertisation of an internal iliac artery and the teachings therein are incorporated herein in their entirety. The aperture and valve arrangement in the tubular body or side arm allows an indwelling catheter to be provided through the sidearm in the iliac artery at the time of deployment to assist with deployment of leg extension into the internal iliac artery.

U.S. patent application Ser. No. 10/962,763 entitled "Introducer for Iliac Side Branch Device" discloses an arrangement for using an indwelling catheter to access an internal iliac artery and the teaching of this specification is incorporated herewith in its entirety.

In this case the indwelling catheter can be extended and its guide wire snared from the contra-lateral artery and the leg extension placed into the ipsilateral internal iliac artery before the leg extension is placed into the contralateral iliac artery.

This then generally describes the invention but to assist with understanding reference will now be made to the accompanying drawings which show further embodiments of the invention.

BRIEF DESCRIPTION OF THE DRAWING

In the drawings;

FIG. 5 shows a tubular body of an alternative embodiment of a stent graft incorporating a side aperture and valve arrangement according to the present invention;

FIG. 6 shows a detail of the valve arrangement of FIG. 5 showing the self expanding stent with a valve member mounted onto it;

FIG. 7 shows a cross section of the embodiment shown in FIG. 5 rotated axially by 45°;

FIG. 8 shows a cross section of the embodiment shown in FIG. 5 rotated axially by 45° with the valve arrangement retracted from the side aperture and a catheter extending through the side aperture;

DETAILED DESCRIPTION

Figures 1, 2:
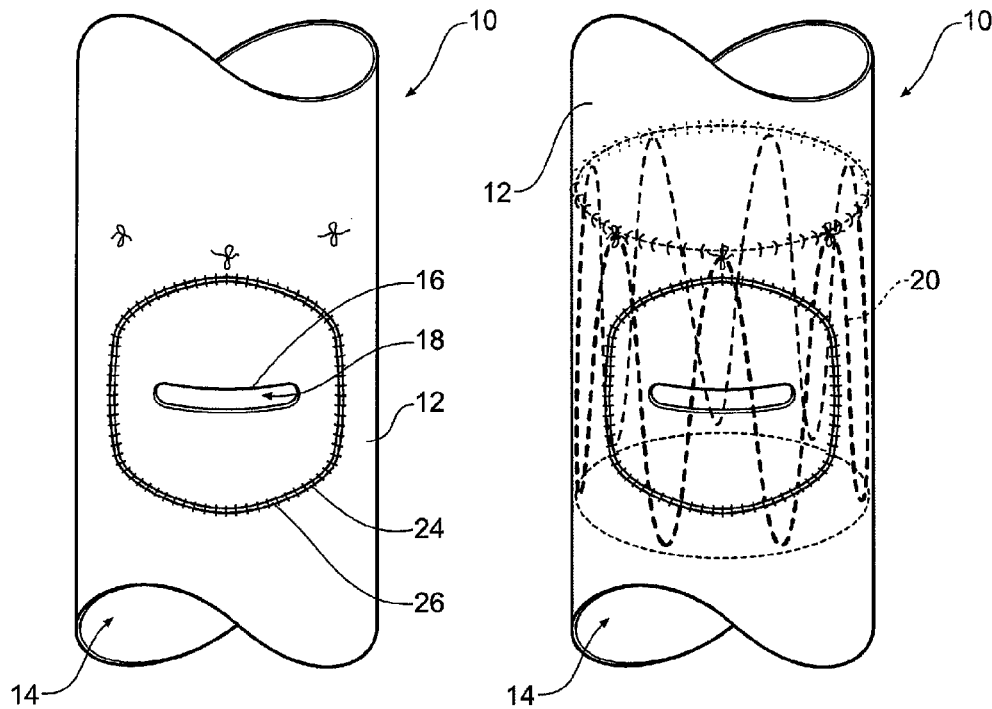
FIG. 1 shows a tubular body of one embodiment of a stent graft incorporating a side aperture and valve arrangement according to the present invention.
FIG. 2 shows the embodiment of FIG. 1 with the internal components shown dotted.
Figures 3, 4:
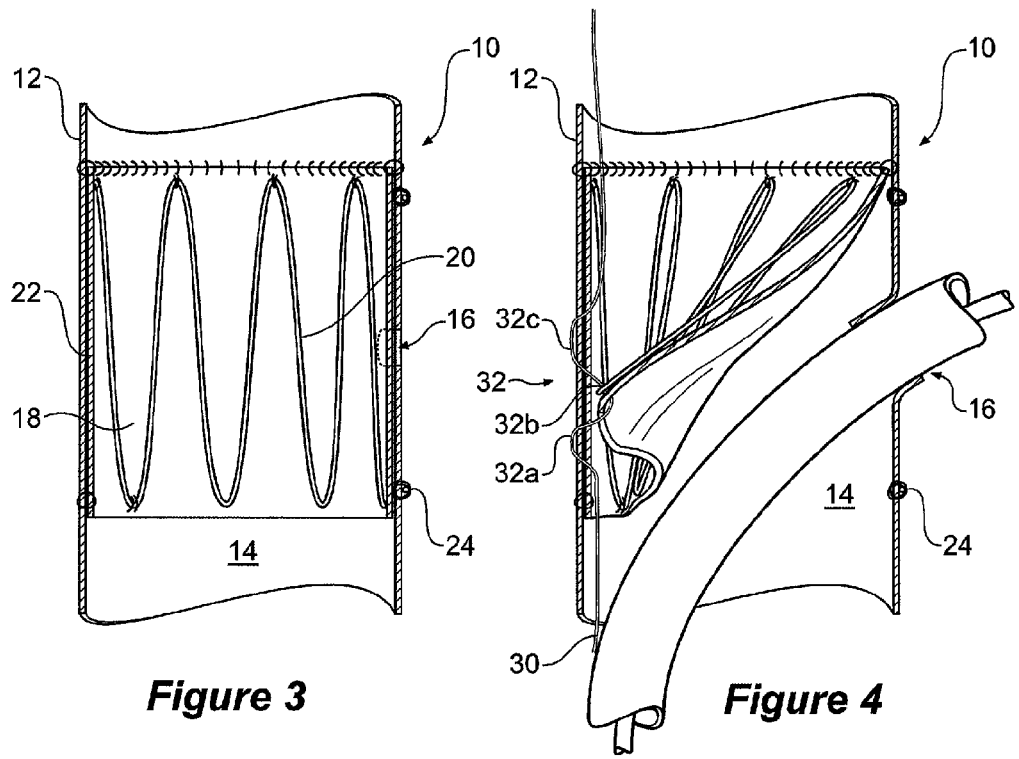
FIG. 3 shows a cross section of the embodiment shown in FIG. 1 rotated axially by 45°.
FIG. 4 shows a cross section of the embodiment shown in FIG. 1 rotated axially by 90° with the valve arrangement retracted from the side aperture and a catheter extending through the side aperture.

Looking more closely at the drawings and in particular FIGS. 1 and 4 show a schematic view of part of a tubular body of one embodiment of a stent graft incorporating a side aperture and valve arrangement according to the present invention.

FIG. 1 shows a tubular body of a stent graft incorporating a side aperture and valve arrangement according to the present invention, FIG. 2 shows a detail of the valve arrangement of FIG. 1, FIG. 3 shows a cross section of the embodiment shown in FIG. 1 and FIG. 4 shows a cross section of the embodiment shown in FIG. 1 with the valve arrangement retracted from the side aperture and a catheter extending through the side aperture.

A stent graft 10 in this embodiment comprises a tubular body 12 of a biocompatible graft material defining a lumen 14 therethrough The tubular body has a side aperture 16 and a valve arrangement 18 associated with the tubular body to prevent fluid flow through the aperture from inside of the tubular to outside of the tubular body. The aperture in this embodiment is a transverse slot which is considerably longer than it is wide. The region of the tubular body around the aperture 16 is reinforced with a substantially circular ring of reinforcement wire 24 spaced away from the aperture and stitched to the tubular body by stitches 26. The reinforcement wire may for instance be formed from nitinol or stainless steel.

The side aperture 16 is preferably of such a length that it can allow a catheter for deploying a side branch leg extension through it as is discussed below. Such a catheter may be a 8 to 10 French catheter. Where the tubular body of the stent graft is formed from a material such as Dacron the edges of the aperture may be heat sealed to prevent unravelling of the weave of the graft material.

The valve arrangement 18 has a self expanding stent 20 and a cylindrical biocompatible graft material sleeve 22. The sleeve 22 engages onto the tubular body 12 around the aperture 16 and acts a valve preventing flow through the valve and the stent 20 holds the sleeve against the tubular body 12 around the aperture 16 as can be particularly seen in the cross sectional view of FIG. 3, for instance. The self expanding stent may for instance be formed from nitinol or stainless steel.

As shown in FIG. 4 the valve arrangement can be held retracted from the aperture 16 to allow unrestricted access for a catheter through the side aperture 16 during deployment of a branch stent graft which will be discussed in more detail below. The valve arrangement is held retracted by a release wire arrangement. A release wire 30 extends through the lumen 14 of tubular body 12 and is stitched into the tubular body at a position 32 substantially opposite to the side aperture 16. The release wire 30 is first stitched onto the tubular body at 32a and then through the valve arrangement at 32b and then through the tubular body again at 32c. By this arrangement the valve is held retracted from the side aperture and movement of a catheter through the aperture is not hindered. The release wire is either engaged with the graft material of the valve sleeve 22, with one or more struts or apex of the stent 20 associated with the valve arrangement or with both of these.

FIG. 5 shows a tubular body of an alternative embodiment of a stent graft incorporating a side aperture and valve arrangement according to the present invention, FIG. 6 shows a detail of the valve arrangement of FIG. 5 showing the self expanding stent with a valve member mounted onto it, FIG. 7 shows a cross section of the embodiment shown in FIG. 5 and FIG. 8 shows a cross section of the embodiment shown in FIG. 5 with the valve arrangement retracted from the side aperture and a catheter extending through the side aperture.

A stent graft 40 in this embodiment comprises a tubular body 42 of a biocompatible graft material defining a lumen 44 therethrough The tubular body has a side aperture 46 and a valve arrangement 48 associated with the tubular body to prevent fluid flow through the aperture from inside of the tubular body to outside of the tubular body. The aperture in this embodiment is a transverse slot which is considerably longer than it is wide.

The valve arrangement has a self expanding stent 50 and a part cylindrical biocompatible graft material sleeve 52 stitched onto struts of the stent. The sleeve 52 engages onto the tubular body 42 around the aperture 46 and acts as a valve preventing flow through the valve and the stent 50 holds the sleeve against the tubular body 42 around the aperture 46 as can be particularly seen in FIG. 7, for instance.

As shown in FIG. 8 the valve arrangement 48 can be held retracted from the aperture 46 to allow unrestricted access for a catheter through the side aperture during deployment of a branch stent graft which will be discussed in more detail below. The valve arrangement is held retracted by a release wire arrangement. A release wire 54 extends through the lumen 44 of tubular body 42 and is stitched into the tubular body at a position 56 substantially opposite to the side aperture 46. The release wire 54 is first stitched onto the tubular body at 56a and then through the valve arrangement at 56b and then through the tubular body again at 56c. By this arrangement the valve is held retracted from the side aperture and movement of a catheter through the aperture is not hindered.

The release wire is either engaged with the graft material of the valve sleeve 52, with one or more struts or apex of the stent 50 associated with the valve arrangement or with any combination of these.

Figure 9:
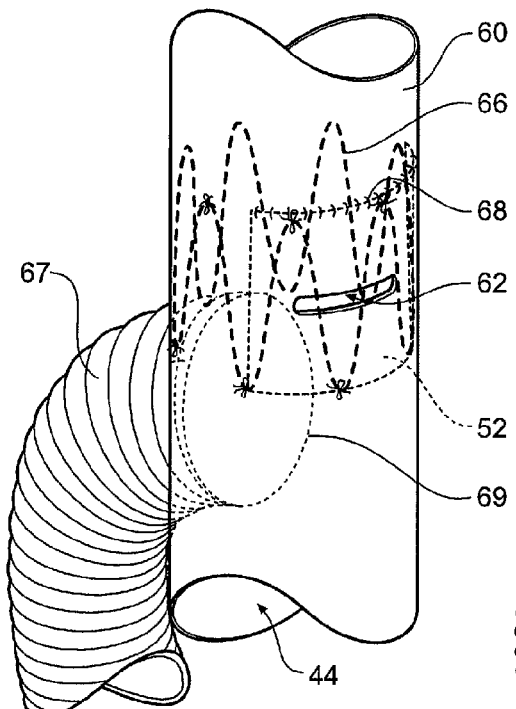
FIG. 9 shows a leg and side arm extending from the leg of a bifurcated stent graft of an alternative embodiment of a stent graft incorporating a side aperture and valve arrangement according to the present invention.
Figure 10:
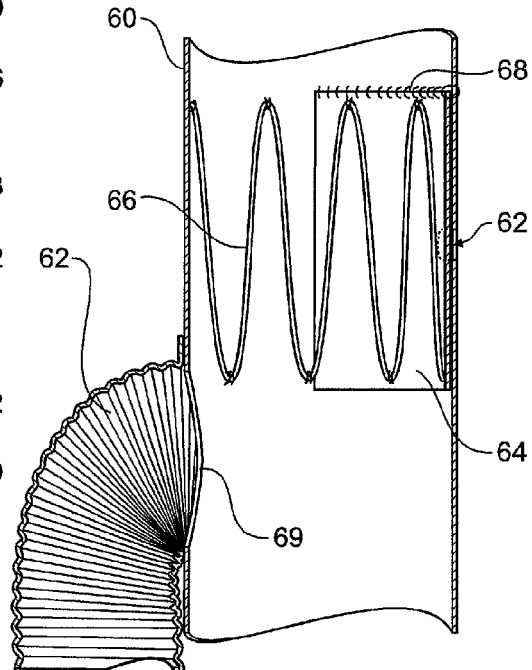
FIG. 10 shows a cross section of the embodiment shown in FIG. 9 rotated axially by 45°.
Figure 11:
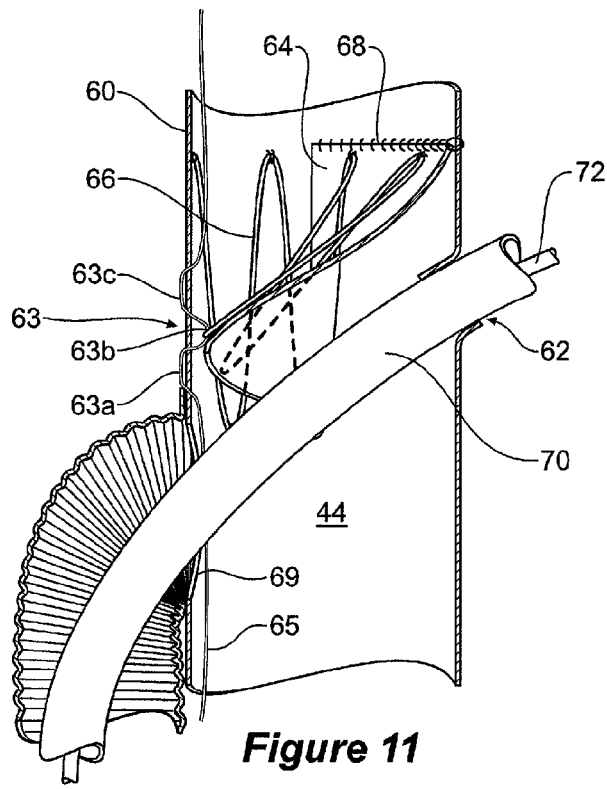
FIG. 11 shows a cross section of the embodiment shown in FIG. 9 rotated axially by 45° with the valve arrangement retracted from the side aperture and a catheter extending through the side aperture.

FIGS. 9, 10 and 11 show a further embodiment of valve arrangement suitable for the present invention.

Figure 12:
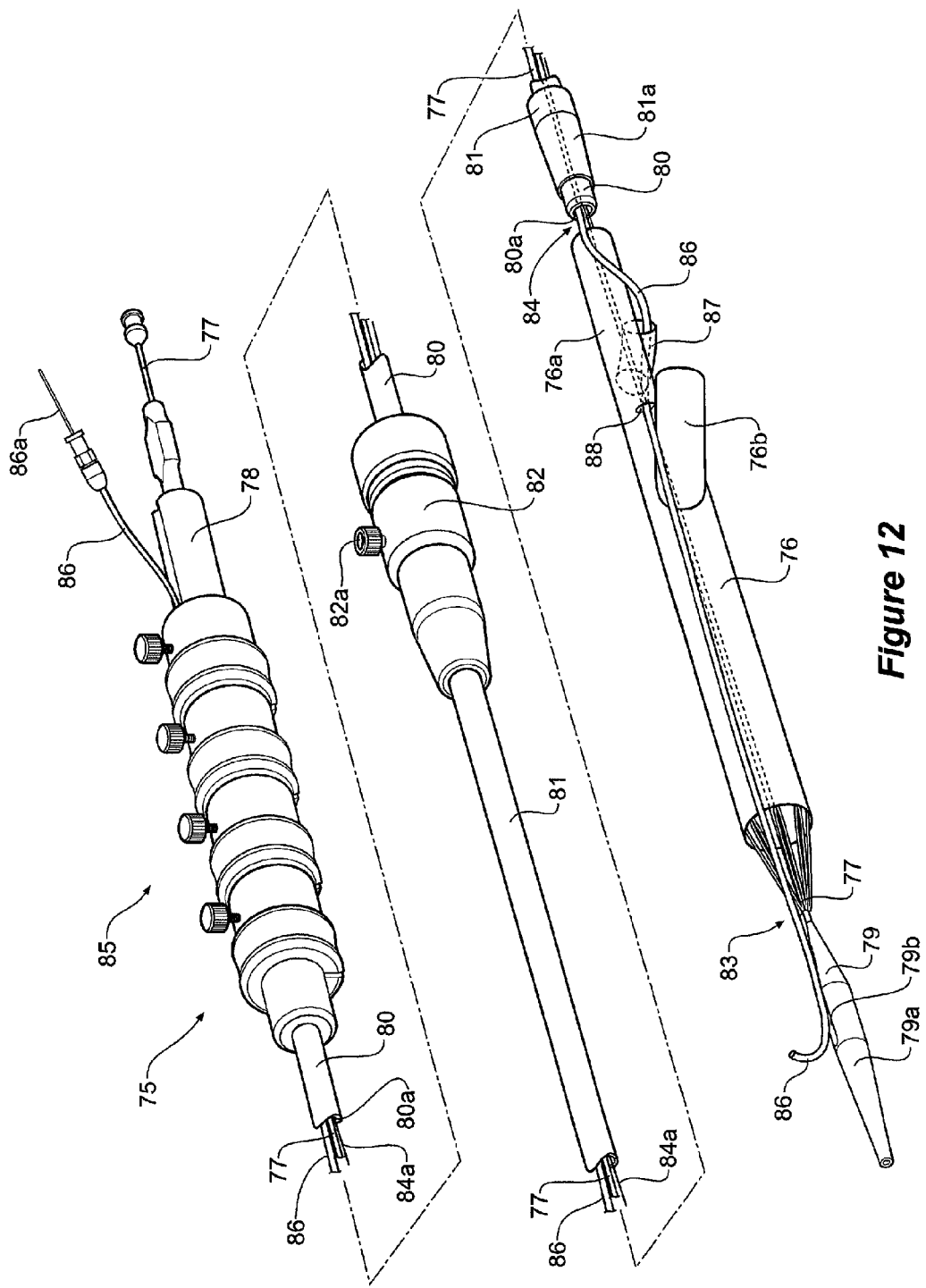
FIG. 12 shows a schematic view of a stent graft loaded onto a delivery device according to the present invention.

In this embodiment part of the longer leg 60 of a bifurcated stent graft, for instance as shown in FIG. 12 below, is shown. The longer leg 60 has an elongate aperture, slit or fenestration 62. Inside the longer leg 60 is a semi-circular portion 64 of biocompatible graft material 52 and a resilient self-expanding zigzag stent 66 which engages with the semi-circular biocompatible graft material 52 and engages it against the inside wall of the longer leg 60 and in particular over the slit or fenestration 62. By this arrangement the slit or fenestration 62 is held in a closed configuration. The semi-circular piece of material 64 is stitched by stitching 68 at its proximal end to the inner wall of the longer leg 60.

Substantially opposite to the elongate slit 62 in the tubular longer leg 60 a side arm 67 extends from a fenestration 69 in the tubular longer leg 60.

FIG. 11 shows the embodiment as shown in FIGS. 9 and 10 except that an indwelling catheter 70 and guide wire 72 through the indwelling catheter extend through the side arm 67 and through the fenestration 69. The semi-circular piece of material 64 is held off the elongate slit against the restoring force of the resilient self expanding stent 66 by a release wire mechanism.

The release wire mechanism comprises a release wire 65 extending from a release mechanism on a delivery device upon (not shown) which the stent graft, of which the long leg 60 is part, is mounted. The release wire 65 extends through the lumen of the long leg 60 and is stitched into the long leg at a position 63 substantially opposite to the side aperture 62. The release wire 65 is first stitched onto the tubular body at 63a and then through the valve arrangement at 63b and then through the tubular body again at 63c. By this arrangement the valve member is held retracted from the side aperture and movement of a catheter through the aperture is not hindered.

The release wire is either engaged with the graft material of the valve sleeve 52, with one or more struts of the stent 66 associated with the valve arrangement or with both of these.

FIG. 12 shows a schematic view of a stent graft 76 loaded onto a delivery device 75 according to the present invention. The delivery device 75 has a guide wire catheter 77 which extends from a distal handle 78 to the proximal tapered nose cone dilator 79 longitudinally through a passageway or lumen 80a of a pusher catheter 80 which is connected to the handle 78 at its distal end. An introducer sheath 81 fits coaxially around the pusher catheter 80 and extends from a tapered proximal end 81a which optionally includes a radiopaque marker to a connector valve and hub 82 attached to the distal end of the sheath. The introducer sheath 81 extends proximally to the nose cone dilator 79 and covers the stent graft 76 during introduction of the deployment device into a patient and is withdrawn distally to expose the stent graft 76 during deployment when the deployment device is in a selected position within the vasculature of a patient. The sheath 81 is shown in the retracted position in FIG. 12.

The stent graft or implantable device 76 is carried on the guide wire catheter 77 proximally of the pusher catheter 80 and distally of the nose cone dilator 79. The stent graft 76 comprises a tubular body of a biocompatible material and a plurality of self expanding stents (not shown for clarity) Towards its distal end the stent graft is bifurcated into a longer leg 76a and a shorter leg 76b. The stent graft includes on the longer leg 76a a side arm which extends part helically around the long leg 76a. A transverse elongate slit aperture 88 is provided in the long leg 76a and a valve arrangement (see FIGS. 1 to 11) is provided to close off the slit aperture.

Connector valve and hub 82 includes a silicone disk assembly (not shown) for preventing the backflow of fluids therethrough. The disk assembly includes a slit for the insertion of the nose cone dilator 79 and delivery catheter 80. Connector and hub 82 also includes side arm 82a to which a tube may be connected for introducing and aspirating fluids therethrough. Nose cone dilator 79 includes a tapered proximal end 79a for accessing and dilating a vascular access site over a well-known and commercially available wire guide (not shown).

The stent graft has a proximal retention arrangement 83 immediately distal of the nose cone dilator 79 on the guide wire catheter 77 and a distal retention arrangement 84 on the long leg 76a at the proximal end of the pusher catheter 80. Release wires extend from each of the proximal and distal retention arrangements to release mechanisms 85 on the handle 78. The release wire 84a for the distal retention 84 also extends to the valve arrangement and holds the valve member off the slit aperture as discussed in relation to and as shown in FIG. 4, for instance.

An indwelling catheter 86 enters the handle 78 and extends through the lumen 80a of the pusher catheter 80 and exits the pusher catheter at its proximal end. The indwelling catheter then extends along and on the outside of the long leg 76a and enters the distal end of the side arm 87 into the lumen of the long leg and then exits the slit aperture 88 and extends along and on the outside of the stent graft 76 to the nose cone dilator 79. The nose cone dilator has a elongate groove 79b in its outer surface and the indwelling catheter extends along the groove. The indwelling catheter 86 has an indwelling guide wire 86a. The indwelling catheter can have a pre-curved proximal end 86b. The pre-curved proximal end of the indwelling catheter having its proximal end in the elongate groove, wherein in a partially retracted position of the introducer sheath the pre-curved proximal end of the indwelling catheter is exposed and in a curved configuration and not covered by the sleeve and in an advanced position of the introducer sheath the pre-curved proximal end of the indwelling auxiliary catheter is in a straightened configuration, extends along the groove in the nose cone and is covered by the introducer sheath. The indwelling guide wire can be extended to be snared from a contra-lateral iliac artery as discussed below.

U.S. patent application Ser. No. 11/600,655 entitled "Stent Graft Introducer" (US Publication 2007/0123910) discusses the use of indwelling catheters with curved proximal ends and the teachings therein are incorporated herein in their entirety.

Figure 13:
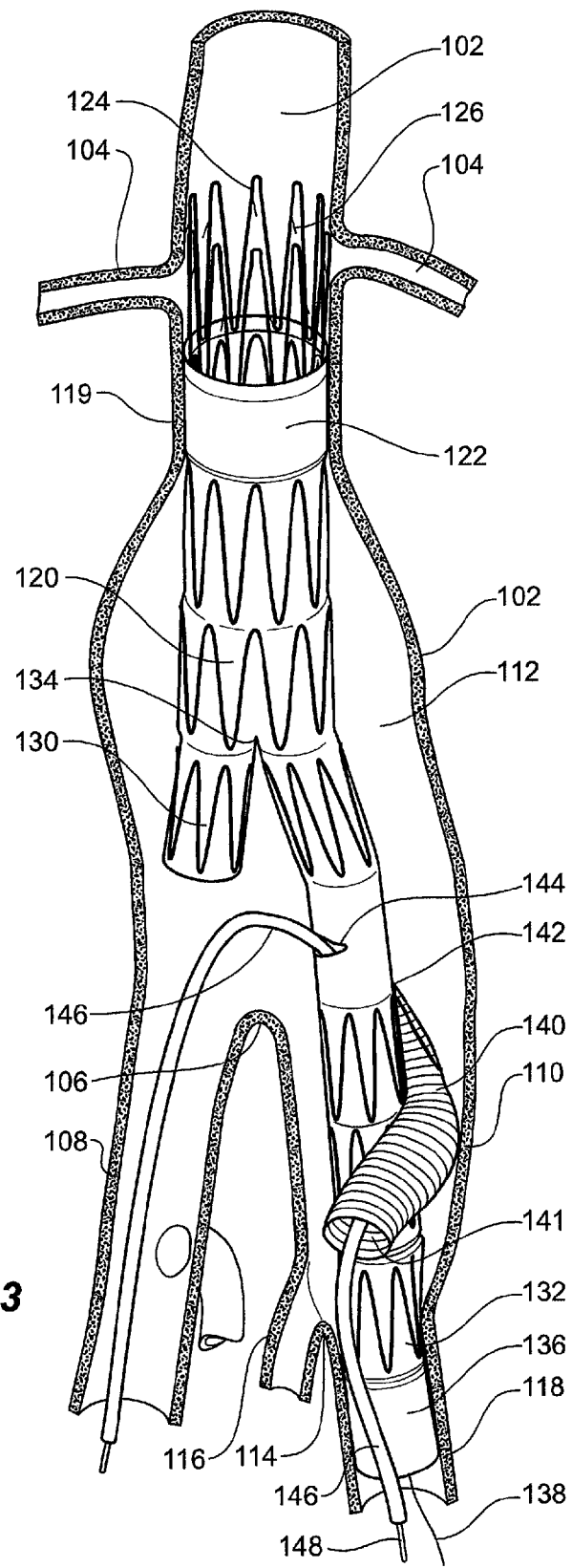
FIG. 13 shows an embodiment of stent graft and indwelling catheter according to the invention deployed into the vasculature before placement of an iliac side branch.

FIG. 13 shows a schematic view of a stent graft with a valve arrangement according to the invention deployed into the vasculature before placement of an iliac side branch. In practice, the stent graft would not be as shown in use because a delivery device would be present but this has been omitted for clarity.

The vasculature comprises an aorta 102 in the region between the renal arteries 104 and the aortic bifurcation 106. Common iliac arteries 108 and 110 extend down from the aortic bifurcation 106. The aorta 102 has an aneurysm 112 which extends down into the common iliac artery 110 as far as the bifurcation 114 between the internal iliac artery 116 and the external iliac artery 118.

To traverse the aneurysm 112 a twin bifurcated aortic stent graft 120 according to one embodiment of the present invention has been deployed into the aorta 102. In this drawing the introduction device which is used to deploy the stent graft into the vasculature has been omitted to assist clarity. In our earlier patent application, PCT Patent Publication No. WO 98/53761 entitled "A prosthesis and a method deploying a prosthesis" there is disclosed an introducer for a stent graft which is suitable for use with the present invention. The proximal end 122 of the bifurcated stent graft 120 is engaged into non-aneurysed portion 119 of the aorta 102 just distal of the renal arteries 104. In this embodiment stent graft 120 has a proximally extending supra-renal exposed stent 124 with barbs 126 engaging the wall of the aorta proximal of the renal arteries to provide a secure position to prevent migration of the stent graft. The stent graft 120 has a short leg 130 and a long leg 132 extending from the graft bifurcation 134. The longer leg 132 has a sealing surface 136 at its distal end which engages into a non-aneurysed portion of the external iliac artery 118.

The longer leg 132 has a side arm 140 which in this embodiment is in the form of a corrugated tube extending in a part helical manner from its connection at a fenestration 142 into the longer leg 132. The side arm 140 extends in a distal direction and helically partly around the longer leg 132 and has a distal end 141 remote from its connection with the longer leg 132 which opens adjacent to the internal iliac artery 116.

A transverse slit 144 is placed into the longer leg 132 in the region of the connection of the side arm 140 into the longer leg 132. The transverse slit 144 has a valve arrangement within it to close it off as discussed above with reference to FIGS. 1 to 11. A release wire 138 extends up through the long leg 132 and engages the valve member within the long leg on the region of the transverse slit 144 and holds the valve member away from the transverse slit as discussed above on relation to FIG. 4, for instance. The release wire 138 extends at its distal end to a release mechanism on a delivery device (see FIG. 12). The release wire 138 may also act as a releasable release mechanism for the distal end of the long leg where it is temporarily retained onto the delivery device.

During deployment of the stent graft into the vasculature of a patient an indwelling catheter 146 extends through the side arm 140 and out through the valved transverse slit 144 as discussed in relation to FIG. 12. The indwelling catheter includes an auxiliary guide wire 148. As illustrated the indwelling catheter is depicted extending down the contra-lateral artery. At this stage the indwelling catheter and guide wire is as described below a through-and-through auxiliary guide wire within the indwelling catheter from one iliac artery to the other.

A process for use of the stent graft and delivery device of the present invention is discussed below.

The various stages of deployment of a stent graft incorporating a valve arrangement according to one embodiment of the present invention are as follows.

A delivery device has a nose cone dilator at its proximal end and a stent graft assembly according to one embodiment of the present invention is mounted onto the deployment device. This embodiment of stent graft has a helical side arm on the longer leg of the stent graft. An indwelling catheter extends from the deployment device through the helical side arm exiting at valved aperture and extending to a groove in the nose cone dilator outside of the stent graft. The indwelling catheter has a flexible curved proximal end. An embodiment of such a stent graft mounted onto a delivery device is shown in FIG. 12.

Details of various embodiments of the tubular side arm and valve arrangement are shown in FIGS. 1 to 11. The tubular side arm 140 extends around the longer leg 132 from a fenestration 142 and the indwelling catheter 146 extends into the tubular side arm and out through the valved aperture 144. The valved aperture 144 has a flap valve on its inside to ensure that the aperture is closed when the indwelling catheter is removed. The flap valve is substantially the same as the as the construction shown in FIGS. 3 to 6.

The deployment device is deployed over a guide wire so that its nose cone extends up into the aneurysm to be spanned and the distal end of the nose cone is substantially adjacent to an aortic bifurcation. The sheath of the deployment device is withdrawn slightly to release the curved tip of the indwelling catheter and the indwelling guide wire from the indwelling catheter is extended. Because of the curved end of the indwelling catheter the indwelling guide wire extends down the contra-lateral iliac artery. A snare catheter is deployed into the contra-lateral common iliac artery and a snare of the snare catheter is extended to grasp the guide wire. The guide wire is extracted via the snare catheter so that it becomes a through-and-through guide wire from one iliac artery to the other. It is important at this stage to ensure there is slack maintained in the guide wire at the aortic bifurcation to prevent damage to the aortic bifurcation.

The use of an indwelling catheter with a curved tip to facilitate snaring from a contra-lateral iliac artery is taught in U.S. patent application Ser. No. 11/600,655 entitled 'Stent Graft Introducer' and the teaching therein is incorporated herein in its entirety.

The deployment device is then advanced so that the nose cone dilator is proximal of the renal arteries. This draws the indwelling guide wire also up into the aorta. The sheath of the deployment device is then withdrawn to release the shorter leg of the stent graft. The indwelling catheter is then withdrawn down into the contra-lateral iliac artery and the sheath is withdrawn so that it is distal of the distal end of the side arm while still retaining the distal end of the longer leg.

A dilator and sheath is then advanced over the guide wire in the contra-lateral iliac artery and the indwelling catheter and extension arm deployment device are tracked over the guide wire so that the nose cone of the dilator enters the valved slit aperture and tracks over the guide wire into the side arm until it exits the distal end of the side arm. The dilator is then withdrawn leaving the sheath in place. At this stage the indwelling guide wire is still in a through-and-through position. A second guide wire is introduced through the sheath and extended from the sheath to enter into the internal iliac artery. A side arm deployment device is then deployed over the second guide wire into the internal iliac artery so that balloon expandable covered stent, for instance, extends into the internal iliac artery from the side arm. The indwelling guide wire is then removed and the position of the distal end of the longer leg is set into the external iliac artery and the balloon expandable covered stent is expanded. The sheath is then withdrawn and the valve release mechanism released so that the valve closes. A leg extension can then placed into the short leg of the graft. The proximal end of the stent graft is also released from the deployment device such that a portion of the graft seals into a non-aneurysed portion of the aorta distal of the renal arteries while an uncovered suprarenal stent extends over the renal arteries to provide secure fixation.

U.S. patent application Ser. No. 11/788,285 entitled "Twin Bifurcated Stent Graft" (US Publication 2007/0250154) discloses methods of deployment of bifurcated stent grafts which have a further bifurcation on one of the bifurcated legs and deployment of a leg extension into such stent grafts and the teachings therein a incorporated herein in their entirety.

Throughout this specification various indications have been given as to the scope of invention but invention not limited to any one of these but may reside in two or more of these combined together. The examples are given for illustration only and not for limitations.

What is claimed is:

1. A stent graft delivery device in combination with a stent graft,
    the stent graft comprising a tubular body of a biocompatible graft material defining a lumen therethrough, the tubular body comprising a side aperture and a valve arrangement associated with the tubular body to prevent fluid flow through the aperture from inside of the tubular body to outside of the tubular body,
    the stent graft delivery device comprising a distal end of the delivery device to remain outside a patient in use and a proximal end of the delivery device to be introduced into a patient in use,
    an arrangement to retain the stent graft on the stent craft delivery device adjacent to the proximal end of the delivery device,
    the distal end of the delivery device comprising a release wire mechanism and a release wire extending from the release wire mechanism towards and into the main lumen of the stent graft and engaging the valve arrangement to hold the valve arrangement away from the side aperture,
    whereby activation of the release wire mechanism retracts the release wire and releases the valve arrangement such that the valve arrangement closes off the side aperture.

2. A stent graft delivery device in combination with a stent graft as in claim 1 wherein the stent graft delivery device comprising a guide wire catheter, the guide wire catheter extending from the distal end of the delivery device to the proximal end of the delivery device,
    a pusher catheter over the guide wire catheter and extending from the distal end of the delivery device to a proximal pusher catheter end, the pusher catheter comprising a pusher lumen and the guide wire catheter extending through the pusher lumen,
    a nose cone dilator on the guide wire catheter at the proximal introducer end and the stent graft being retained on the introducer device distally of the nose cone dilator and proximally of the proximal pusher end,
    the release wire mechanism extending through the pusher lumen and into the main lumen of the stent graft to engage the valve arrangement.

3. A stent graft delivery device in combination with a stent graft as in claim 1 wherein the side aperture comprises a transverse slit in the tubular body.

4. A stent graft delivery device in combination with a stent graft as in claim 1 wherein the valve arrangement comprises a sleeve of a biocompatible graft material within the tubular body and a self expanding stent within the sleeve, the sleeve being fastened at its proximal end to the tubular body proximally of the aperture and the self expanding stent being fastened to the sleeve, whereby the self expanding stent forces the sleeve against an inner surface of the tubular body around the aperture to prevent fluid flow through the aperture from inside of the tubular body to outside of the tubular body.

5. A stent graft delivery device in combination with a stent graft as in claim 4 wherein the sleeve of a biocompatible graft material comprises a cylindrical form.

6. A stent graft delivery device in combination with a stent graft as in claim 4 wherein the sleeve of a biocompatible graft material comprises a semi-cylindrical form.

7. A stent graft delivery device in combination with a stent graft as in claim 1 wherein the valve arrangement comprises a valve assembly comprising a self expanding stent to which a part cylindrical portion of biocompatible graft material is stitched along spaced apart struts of the self expanding stent, the self expanding stent and sleeve being fastened at their proximal ends to the tubular body proximally of the aperture.

8. A stent graft delivery device in combination with a stent graft as in claim 1 wherein the engagement of the release wire with the valve arrangement comprises the release wire being stitched into the graft material of the tubular body and then into the valve arrangement and then into the graft material of the tubular body again.

9. A stent graft delivery device in combination with a stent graft as in claim 8 wherein the engagement of the release wire with the graft material of the tubular body comprises stitching the release wire into the graft material at a position on the tubular body substantially opposite to the side aperture.

10. A stent graft delivery device in combination with a stent graft as in claim 8 wherein the valve arrangement comprises a self expanding stent and a sleeve of biocompatible graft material and the engagement of the release wire with the valve arrangement comprises stitching the release wire around a strut or apex of the self expanding stent.

11. A stent graft delivery device in combination with a stent graft,
the stent graft comprising a tubular body of a biocompatible graft material defining a main lumen therethrough, a bifurcation in the tubular body at one end thereof and a first leg and a second leg extending from the bifurcation, the first leg being a long leg and the second leg being a short leg, the first and second legs having respective first and second lumens therethrough and the first and second lumens being in fluid communication with the main lumen, the first leg comprising a side arm with a side arm lumen therethrough and the side arm lumen being in fluid communication with the first leg lumen, the first leg comprising a side aperture and a valve arrangement to prevent fluid flow through the aperture from inside of the leg to outside of the leg, the side aperture comprising a transverse slit,
the stent graft delivery device comprising a distal end intended to remain outside a patient in use and a proximal end to be introduced into a patient in use, the stent graft delivery device comprising a guide wire catheter, the guide wire catheter extending from a distal introducer end to a proximal introducer end, a pusher catheter over the guide wire catheter and extending from the distal introducer end to a proximal pusher end, the pusher catheter comprising a pusher lumen and the guide wire catheter extending through the pusher lumen, a nose cone dilator on the guide wire catheter at the proximal introducer end and an arrangement to retain the stent graft on the introducer device distally of the nose cone dilator and proximally of the proximal pusher end,
the guide wire catheter extending through the first leg lumen and the main lumen of the main tubular body, the distal end of the delivery device comprising a release wire mechanism and a release wire extending from the release wire mechanism through the pusher lumen and into the first lumen of the stent graft and engaging the valve arrangement to hold the valve arrangement away from the side aperture,
whereby activation of the release wire mechanism retracts the release wire and releases the valve arrangement such that the valve arrangement closes off the side aperture.

12. A stent graft delivery device in combination with a stent graft as in claim 11 wherein the valve arrangement comprises a sleeve of a biocompatible graft material within the first leg and a self expanding stent within the sleeve, the sleeve being fastened at its proximal end to the first leg proximal of the aperture and the self expanding stent being fastened to the sleeve, whereby the self expanding stent forces the sleeve against the inner surface of the first leg around the aperture to prevent fluid flow through the aperture from inside of the leg to outside of the leg.

13. A stent graft delivery device in combination with a stent graft as in claim 12 wherein the sleeve of a biocompatible graft material comprises a cylindrical form.

14. A stent graft delivery device in combination with a stent graft as in claim 12 wherein the sleeve of a biocompatible graft material comprises a semi-cylindrical form.

15. A stent graft delivery device in combination with a stent graft as in claim 11 wherein the valve arrangement comprises a valve assembly comprising a self expanding stent to which a part cylindrical portion of biocompatible graft material is stitched along spaced apart struts of the self expanding stent, the self expanding stent and sleeve being fastened at their proximal ends to the tubular body proximally of the aperture.

16. A stent graft delivery device in combination with a stent graft as in claim 11 wherein the engagement of the release wire with the valve arrangement comprises the release wire being stitched into the graft material of the first leg and then into the valve arrangement and then into the graft material of the first leg again.

17. A stent graft delivery device in combination with a stent graft as in claim 16 wherein the engagement of the release wire with the graft material of the first leg comprises stitching the release wire into the graft material at a position on the first leg substantially opposite to the side aperture.

18. A stent graft delivery device in combination with a stent graft as in claim 16 wherein the valve arrangement comprises a self expanding stent and a sleeve of biocompatible graft material and the engagement of the release wire with the valve arrangement comprises stitching the release wire around a strut or apex of the self expanding stent.

19. A stent graft delivery device in combination with a stent graft as in claim 11 further including an indwelling catheter extending from the distal introducer end through the pusher lumen in the pusher catheter to the stent graft,
the indwelling catheter exiting from the pusher lumen at a distal end of the branched stent graft, the indwelling catheter then extending along and outside of the first long leg of the stent graft and then entering the distal open end of the side arm, the indwelling catheter then extending through the side arm lumen to the first leg lumen and then extending out of the side aperture and then extending outside and along the tubular body of the stent graft to the nose cone dilator, the indwelling catheter having an indwelling guide wire extending therethrough, whereby the indwelling guide wire can be extended beyond the nose cone dilator in use.

20. A stent graft delivery device in combination with a stent graft,
- the stent graft comprising a tubular body of a biocompatible graft material defining a main lumen therethrough, a bifurcation in the tubular body at one end thereof and a first leg and a second leg extending from the bifurcation, the first leg being a long leg and the second leg being a short leg, the first and second legs having respective first and second lumens therethrough and the first and second lumens being in fluid communication with the main lumen, the first long leg comprising a side arm with a side arm lumen therethrough and the side arm lumen being in fluid communication with the first leg lumen, the first leg comprising a side aperture and a valve arrangement to prevent fluid flow through the aperture from inside of the leg to outside of the leg, the side aperture comprising a transverse slit, the valve arrangement comprising a self expanding stent and a sleeve of biocompatible graft material;
- the stent graft delivery device comprising a distal end intended to remain outside a patient in use and a proximal end to be introduced into a patient in use, the stent graft delivery device comprising a guide wire catheter, the guide wire catheter extending from a distal introducer end to a proximal introducer end, a pusher catheter over the guide wire catheter and extending from the distal introducer end to a proximal pusher end, the pusher catheter comprising a pusher lumen and the guide wire catheter extending through the pusher lumen, a nose cone dilator on the guide wire catheter at the proximal introducer end and an arrangement to retain the stent graft on the introducer device distally of the nose cone dilator and proximally of the proximal pusher end,
- the guide wire catheter extending through the first leg lumen and the main lumen of the main tubular body,
- an indwelling catheter extending from the distal introducer end through the pusher lumen in the pusher catheter to the stent graft,
- the indwelling catheter exiting from the pusher lumen at a distal end of the branched stent graft, the indwelling catheter then extending along and outside of the first long leg of the stent graft and then entering the distal open end of the side arm, the indwelling catheter then extending through the side arm lumen to the first leg lumen and then extending out of the side aperture and then extending outside and along the tubular body of the stent graft to the nose cone dilator, the indwelling catheter having an indwelling guide wire extending therethrough, whereby the indwelling guide wire can be extended beyond the nose cone dilator in use,
- the distal end of the delivery device comprising a release wire mechanism and a release wire extending from the release wire mechanism through the pusher lumen and into the first lumen of the stent graft and engaging the valve arrangement to hold the valve arrangement away from the side aperture,
- the engagement of the release wire with the valve arrangement comprises the release wire being stitched into the graft material of the first leg and then into the valve arrangement or around a strut or apex of the self expanding stent and then into the graft material of the first leg again
- whereby activation of the release wire mechanism retracts the release wire and releases the valve arrangement such that the valve arrangement closes off the side aperture.

* * * * *